(12) United States Patent
Welsford et al.

(10) Patent No.: US 11,938,302 B2
(45) Date of Patent: Mar. 26, 2024

(54) METHOD FOR CONTROLLING ARTIFICIAL PANCREAS INCLUDING INSULIN PATCH AND DEVICE THEREFOR

(71) Applicant: EOFLOW CO., LTD., Seongnam-si (KR)

(72) Inventors: Ian G. Welsford, Stratham, NH (US); Inwook Bin, Yongin-si (KR); Ho Min Jeon, Yongin-si (KR)

(73) Assignee: EOFLOW CO., LTD., Seongnam-si (KR)

( * ) Notice: Subject to any disclaimer, the term of this patent is extended or adjusted under 35 U.S.C. 154(b) by 0 days.

(21) Appl. No.: 18/033,137

(22) PCT Filed: Oct. 14, 2021

(86) PCT No.: PCT/KR2021/014267
§ 371 (c)(1),
(2) Date: Apr. 21, 2023

(87) PCT Pub. No.: WO2022/092637
PCT Pub. Date: May 5, 2022

(65) Prior Publication Data
US 2023/0347051 A1    Nov. 2, 2023

(30) Foreign Application Priority Data
Oct. 30, 2020   (KR) ........................ 10-2020-0142657

(51) Int. Cl.
*A61M 5/172*   (2006.01)
*A61M 5/142*   (2006.01)
(Continued)

(52) U.S. Cl.
CPC ...... *A61M 5/1723* (2013.01); *A61M 5/14248* (2013.01); *G06N 3/045* (2023.01);
(Continued)

(58) Field of Classification Search
None
See application file for complete search history.

(56) References Cited

U.S. PATENT DOCUMENTS

2011/0098638 A1*   4/2011   Chawla ................. A61M 5/168
                                                 700/282

FOREIGN PATENT DOCUMENTS

JP    2014524791 A    9/2014
KR    1020110100227   9/2011
(Continued)

OTHER PUBLICATIONS

International Search Report dated Feb. 9, 2022, issued in International Patent Application No. PCT/KR2021/014267.
(Continued)

*Primary Examiner* — Manuel A Mendez
(74) *Attorney, Agent, or Firm* — PNKIP LLC

(57) ABSTRACT

An insulin patch control method and a device therefor are provided. An insulin patch control method and a device therefor are provided. The insulin patch control method according to one embodiment of the present invention comprises the steps of: obtaining, from an insulin patch, blood glucose information measured by a blood glucose sensor; inputting the obtained blood glucose information into a first neural network; estimating a pump parameter of the insulin patch on the basis of output data of the first neural network; and simulating the insulin patch by inputting the blood sugar information and the pump parameter into a second neural network.

5 Claims, 7 Drawing Sheets

(51) Int. Cl.
G06N 3/045 (2023.01)
G06N 3/08 (2023.01)
G16H 20/17 (2018.01)
G16H 40/67 (2018.01)
G16H 50/20 (2018.01)

(52) U.S. Cl.
CPC ............... G06N 3/08 (2013.01); G16H 20/17 (2018.01); G16H 40/67 (2018.01); G16H 50/20 (2018.01); *A61M 2005/14208* (2013.01); *A61M 2202/0486* (2013.01)

(56) References Cited

FOREIGN PATENT DOCUMENTS

| | | |
|---|---|---|
| KR | 1020110100227 A | 9/2011 |
| KR | 1020160043854 A | 4/2016 |
| KR | 1020170088177 | 8/2017 |
| KR | 1020170088177 A | 8/2017 |
| KR | 1020200119216 | 10/2020 |
| KR | 1020200119216 A | 10/2020 |

OTHER PUBLICATIONS

Non-Final Office Action dated Aug. 3, 2022, issued in Korean Patent Application No. 10-2020-0142657.
Notice of Allowance dated Jan. 18, 2023, issued in Korean Patent Application No. 10-2020-0142657.

\* cited by examiner

METHOD FOR CONTROLLING ARTIFICIAL PANCREAS INCLUDING INSULIN PATCH AND DEVICE THEREFOR

CROSS-REFERENCE TO RELATED APPLICATIONS

This application is a National Stage Entry of International Patent Application No. PCT/KR2021/014267, fled on Oct. 14, 2021, which claims priority from and the benefit of Korean Patent Application No. 10-2020-0142657, filed on Oct. 30, 2020, each of which is hereby incorporated by reference for all purposes as if fully set forth herein.

BACKGROUND

Field

The present disclosure relates to an insulin patch control method and a device therefor. More specifically, the present disclosure relates to a method of controlling an insulin patch by using a pump parameter of the insulin patch obtained by using an artificial neural network.

Discussion of the Background

Development of an insulin injector used by diabetic patients has been actively carried out. Diabetic patients inject insulin into the body through an insulin pen or an insulin pump, but there is an issue that activity in everyday life greatly degrades.

Accordingly, a smart insulin patch has been developed, but there are limitations such as excessive cost, difficulty in continuous data management, and difficulty in real-time blood sugar management. Moreover, because there is a risk that may occur when blood sugar is controlled independently by an insulin patch, a technology capable of addressing the above issue is necessary.

The above information disclosed in this Background section is only for understanding of the background of the inventive concepts, and, therefore, it may contain information that does not constitute prior art.

SUMMARY

One or more embodiments of the present disclosure provide an insulin patch control method and a device therefor, capable of securing high accuracy and stability.

According to an embodiment of the present disclosure, an insulin patch control method, performed in an insulin patch including an insulin pump and a blood sugar sensor, includes obtaining blood sugar information from the blood sugar sensor, estimating a pump parameter of the insulin patch based on the obtained blood sugar information, and transmitting a control signal to the insulin pump based on the estimated pump parameter;

According to another embodiment of the present disclosure, an insulin patch control method, performed by a computing device, includes obtaining blood sugar information measured by a blood sugar sensor, from the insulin patch, inputting the obtained blood sugar information to a first neural network, estimating a pump parameter of the insulin patch based on output data from the first neural network, and performing a simulation of the insulin patch by using the blood sugar information and the pump parameter.

In an embodiment, the inputting of the obtained blood sugar information into the first neural network includes transmitting the obtained blood sugar information to an external server, and receiving a feedback signal as to an effectiveness of the blood sugar information from the external server, and the performing of the simulation of the insulin patch by using the blood sugar information and the pump parameter includes transmitting a simulation result of the insulin patch to the external server, and receiving a feedback signal as to the simulation result of the insulin patch from the external server.

Other aspects, features and advantages other than those described above will become apparent from the following detailed description of the drawings, claims and disclosure.

It is to be understood that both the foregoing general description and the following detailed description are illustrative and explanatory and are intended to provide further explanation of the invention as claimed.

BRIEF DESCRIPTION OF DRAWINGS

The accompanying drawings, which are included to provide a further understanding of the invention and are incorporated in and constitute a part of this specification, illustrate illustrative embodiments of the invention, and together with the description serve to explain the inventive concepts.

Figure 1:
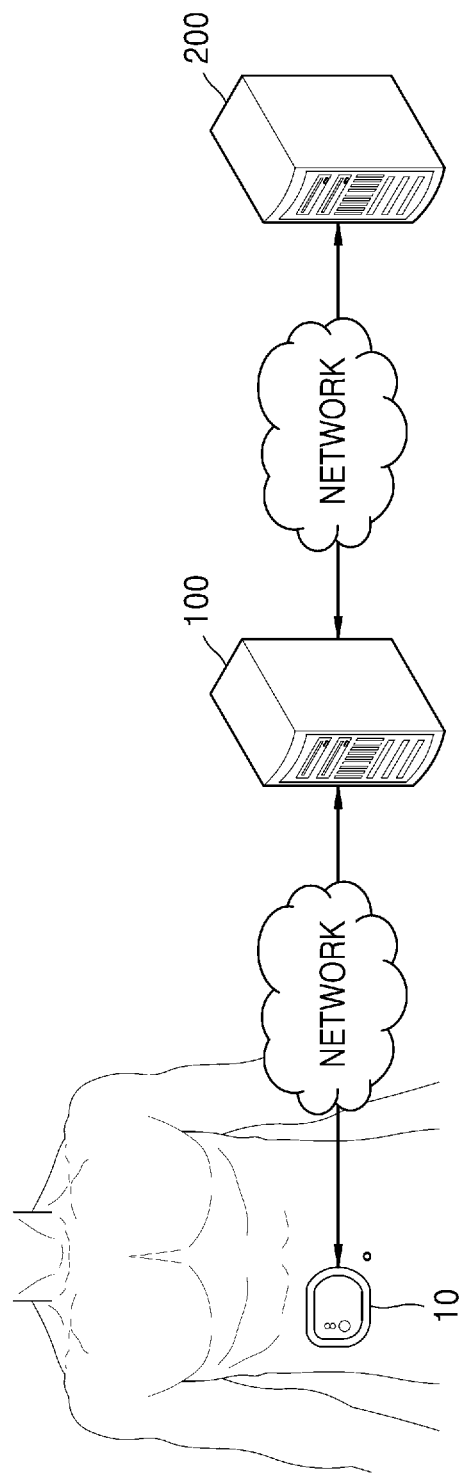
FIG. 1 is a diagram showing an example of an insulin patch control system according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

DETAILED DESCRIPTION

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

The detailed description of the present disclosure which follows refers to the accompanying drawings which illustrate, by way of illustration, specific embodiments in which the present disclosure may be embodied. Such embodiments are described in sufficient detail to enable one of ordinary skill in the art to implement the present disclosure. It should be understood that the various embodiments of the present disclosure are different from each other but are not necessarily mutually exclusive. For example, specific shapes, structures, and features described in one exemplary embodiment may be modified in another exemplary embodiment within the scope of the present disclosure. In addition, the positions or arrangement of elements described in one exemplary embodiment may be changed in another exemplary embodiment within the scope of the present disclosure. Therefore, the detailed description provided hereinafter of the present disclosure shall not be limited, and the entire scope of the appended claims and their equivalents will fall within the scope and spirit of the disclosure. In the drawings, like or similar reference numerals denote like or similar elements.

In the specification, artificial intelligence (AI) may denote a field of researching AI or a methodology capable of making AI, and machine learning is a field of AI technology, that is, a technical method for a computing device to learn through data and to understand certain objects or conditions or to find data patterns and classify the patterns, e.g., an algorithm allowing a computer to analyze data. In the present disclosure, machine teaming may be understood as including an operating method for learning an AI model.

To allow those skilled in the art to the present disclosure to be carried out easily, the various embodiments of the present disclosure by referring to attached diagrams will be explained in detail as shown below.

Hereinafter, an insulin patch control system according to an embodiment of the present disclosure will be described in detail with reference to FIG. 1.

In an embodiment, the insulin patch control system may include an insulin patch alone, or may include the insulin patch 10 and an insulin patch control device 100. Alternatively, in another embodiment, the insulin patch system may include the insulin patch 10, the insulin patch control device 100, and a medical service providing server 200.

In an embodiment, the insulin patch 10 may include an insulin pump for injecting insulin into a human body and a blood sugar sensor for measuring human blood sugar. For example, the insulin patch is an automatic insulin injector in the form of a wearable device and may be a kind of wearable artificial pancreas device. In addition, the insulin patch 10 may independently determine an insulin injection amount without communicating with an external device, according to a method described later with reference to FIG. 5.

In an embodiment, the insulin patch 10 may include a blood sugar measurement sensor for measuring blood sugar. In the present embodiment, the insulin patch 10 may obtain a pump parameter through a pre-designated algorithm based on blood sugar information obtained through the blood sugar measurement sensor. After that, the insulin patch 10 may independently perform insulin patch control using the pump parameter described above.

In an embodiment, the insulin patch control device 100 may communicate with the insulin patch 10 through a network. The above communication method between the insulin patch control device 100 and the insulin patch 10 is not restricted. The above network may be a near field wireless communication network according to an embodiment. For example, the network may be a Bluetooth, Bluetooth Low Energy (BLE), or Wi-Fi communication network.

In an embodiment, the insulin patch control device 100 may obtain blood sugar information from the insulin patch 10 and may estimate a pump parameter for determining an insulin injection amount of the insulin patch 10 by using the obtained blood sugar information. In this case, the insulin patch control device 100 may estimate the pump parameter through a neural network, by using the above blood sugar information.

After that, the insulin patch control device 100 may transmit the estimated pump parameter to the insulin patch 10 and obtain control result data of the insulin patch from the insulin patch 10. The type and kind of the control result data of the insulin patch according to one or more embodiments of the present disclosure are not restricted, and the control result data of the insulin patch in an embodiment may include the above pump parameter and blood sugar information corresponding to the pump parameter. Moreover, the above control result data may include time-serial data including blood sugar information over time. After that, the insulin patch control device 100 may estimate pathology diagnosis result data of a user of the insulin patch by using the estimated pump parameter and the obtained control result data of the insulin patch.

Also, in an embodiment, the insulin patch control device 100 may estimate the pump parameter of the insulin patch 10 by using the neural network, and may select a final pump parameter according to a designated criterion after clustering output data from the neural network. In this case, the insulin patch control device 100 may perform a simulation of the insulin patch 10 based on the selected pump parameter.

That is, in the present embodiment, the insulin patch control device 100 performs a simulation through an insulin injection algorithm by using the pump parameter, and after that, may transfer the pump parameter to the insulin patch 10 only when a validity of the corresponding pump parameter is verified, in order to improve stability.

In another embodiment, the insulin patch control device 100 may estimate the pump parameter described above by further using user information of the insulin patch. In the present embodiment, the insulin patch control device 100 may store past insulin patch usage history information of the user who uses the insulin patch, and may obtain the previous pathology diagnosis result data of the user from the medical service providing server 200. As such, the insulin patch control device 100 may estimate the personalized pump parameter of the insulin patch based on the user information.

Moreover, according to an embodiment, the medical service providing server 200 connected to the insulin patch control device 100 via the network may perform an effectiveness verification of the algorithm that estimates the pump parameter of the insulin patch, and may perform verification of the result of the above-mentioned simulation.

In an embodiment, the medical service providing server 200 may estimate the pathology diagnosis result data of the insulin patch user, instead of the insulin patch control device 100 described above. In an embodiment, the medical service providing server 200 may estimate the pathology diagnosis result data of the insulin patch user by using the blood sugar information obtained from the insulin patch 10, the pump parameter of the insulin patch 10, and the control result data of the insulin patch 10. For example, the medical service providing server 200 may input the blood sugar information, the pump parameter, and the insulin patch control result data to an artificial neural network, and may estimate pathology diagnosis result data by using the artificial neural network. The kind and type of the pathology diagnosis result data are not restricted. For example, the pathology diagnosis result data according to an embodiment may include diagnosis result of diabetes.

After that, the medical service providing server 200 according to an embodiment may receive an input of a feedback signal from the user with respect to the estimated pathology diagnosis result data. In this case, the user may be a medical staff providing medical services. After that, the medical service providing server 200 may perform re-learning and/or estimation by inputting pathology diagnosis result data that is corrected according to the feedback signal of the user into the neural network. By repeating the above processes, the accuracy of the user's pathology diagnosis result data estimated by the medical server providing server 200 according to an embodiment of the present disclosure may be improved.

Hereinafter, configuration and operations of hardware included in the insulin patch control system will be described in detail below with reference to FIG. 2.

As described above, the insulin patch control system according to an embodiment includes the insulin patch 10, may further include the insulin patch control device 100 according to another embodiment, and may further provide the medical service providing server 200 in some other embodiments.

In an embodiment, the insulin patch 10, the insulin patch control device 100 and the medical service providing server 200 may respectively include input/output interfaces 11, 101, 201, memories 12, 102, 202, processors 13, 103, 203, and communication modules 14, 104, 204. The memory 12, 102, or 202 is a computer-readable recording medium, and may include random access memory (RAM), read only memory (ROM), and a permanent mass storage device such as a disk drive. For example, the memory 12 of the insulin patch 10 may temporarily or permanently store the blood sugar information and/or pump parameter information, and the memory 102 of the insulin patch control device 100 may store blood sugar information per user and/or pump parameter information of the insulin patch. Alternatively, in an embodiment, the memory 202 of the medical service providing server 200 may store pathology diagnosis result data of the user.

The processor 13, 103, or 203 may be configured to process commands of a computer program by performing basic arithmetic operations, logic operations, and I/O operations. A command may be provided to the processors 13, 103, and 203 by the memories 12, 102, and 202 or the communication modules 14, 104, and 204. For example, processors 13, 103, and 203 may be configured to execute commands that are received according to a program code stored in a recording device such as the memories 12, 102, and 202. In an embodiment, the processor 103 of the insulin patch control device 100 obtains blood sugar information from the insulin patch 10, inputs the blood sugar information obtained as above into a first neural network, estimates the pump parameter of the insulin patch based on output data from the first neural network, transmits a control signal to the insulin patch based on the estimated pump parameter, obtains control result data from the insulin patch 10, inputs the blood sugar information, the pump parameter, and the control result data to a second neural network, and may estimate the pathology diagnosis result data of the user of the insulin patch based on output data from the second neural network.

The communication modules 14, 104, and 204 may provide communicating function via the network. For example, a request generated by the processor 103 of the insulin patch control device 100 according to program code stored in a storage device such as the memory 102 may be transferred to the insulin patch 10 via the network according to control of the communication module 104. In addition, control signals, commands, content, files, etc. provided under the control of the processor 203 of the medical service providing server 200 may be transferred to the insulin patch control device 100 through the communication module 104 over a network. Moreover, the control signal or command of the medical service providing server 200 received through the communication module 104 of the insulin patch control device 100 may be transferred to the processor 103 or the memory 102 of the insulin patch control device 100, and blood sugar information and/or control result data from the insulin patch 10 may be stored in a storage medium that may be further included in the insulin patch control device 100. Also, the communication method of the communication module 14, 104, and 204 is not limited, but the network may be a near field wireless communication network. For example, the network may include a Bluetooth, Bluetooth Low Energy (BLE), or Wi-Fi communication network.

Also, the input/output interfaces 11, 101, and 201 may receive an input from the user and may display output data. The input/output interface 11 of the insulin patch 10 according to an embodiment may receive an input signal from the user and may display operation information, etc. of the insulin patch on a display. Also, in an embodiment, the input/output interface 201 of the medical service providing server 200 may receive a user's feedback signal and output the control result data of the insulin patch 10.

Figure 2:
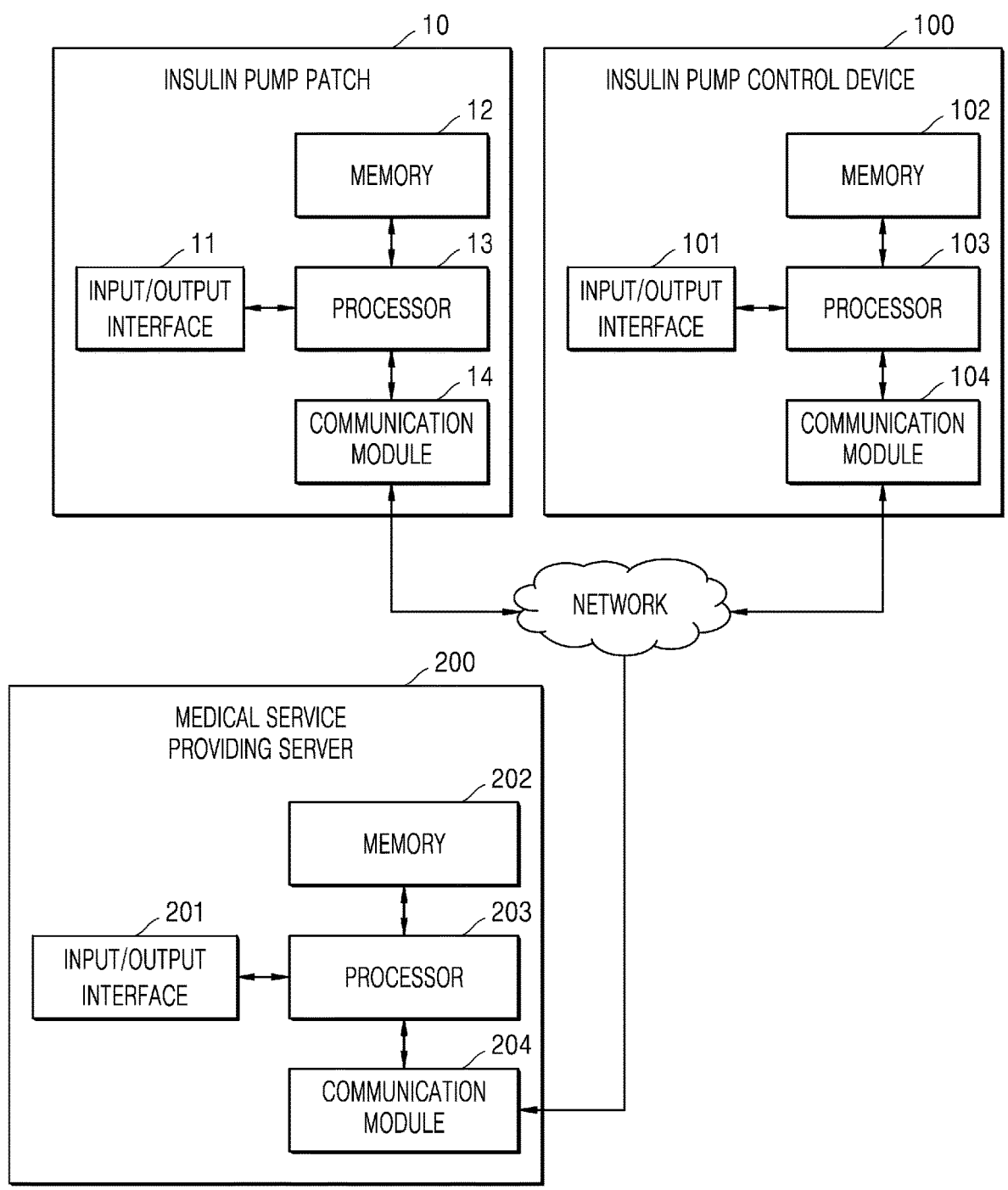
FIG. 2 is a block diagram for describing an internal structure of an insulin patch control device according to an embodiment of the present disclosure.

Also, in other embodiments, the insulin patch 10, the insulin patch control device 100, and the medical service providing server 200 may include more components than those of FIG. 2. However, there is no need to clearly show most of the related art components. For example, the insulin patch control device 100 may include a battery and a charging device that supplies electric power to internal components of a user terminal, and may be implemented to include at least some of the above-described input/output devices or other components such as a transceiver, a global positioning system (GPS) module, various sensors, a database, etc. Also, although not shown in FIG. 2, the insulin patch 10 may include a blood sugar measurement sensor for measuring a blood sugar level, and may further include an insulin injection tube in another embodiment.

Figure 3:
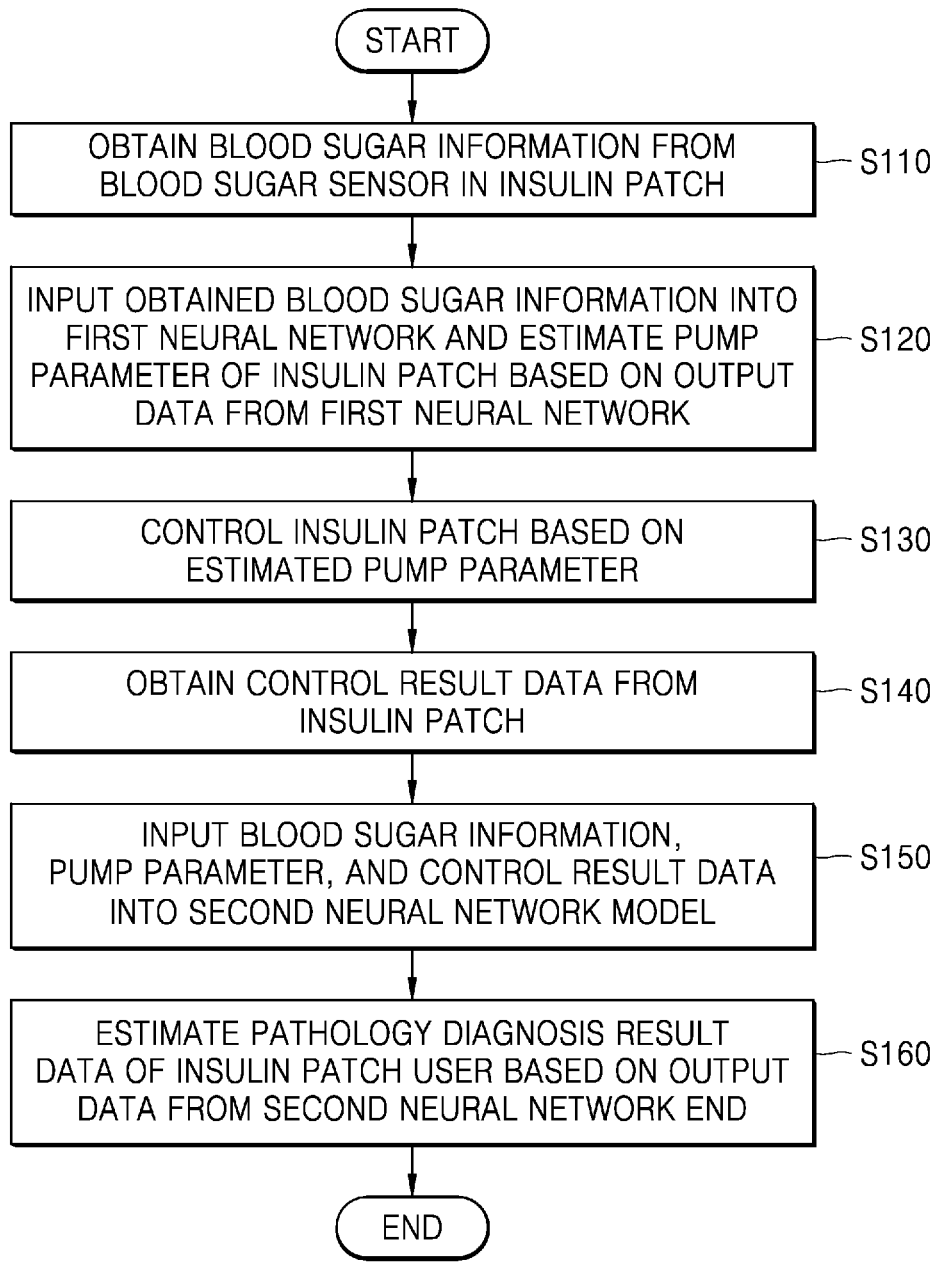
FIG. 3 is a flowchart illustrating an insulin patch control method according to an embodiment of the present disclosure.

FIG. 3 is a diagram for describing an insulin patch control method according to an embodiment of the present disclosure.

In operation S110, an insulin patch control device may obtain blood sugar information from a blood sugar sensor of an insulin patch. In an embodiment, the insulin patch may obtain blood sugar information of the user via the blood sugar sensor. The kind of the blood sugar sensor according to some embodiments of the present invention is not restricted, for example, the blood sugar sensor may be a continuous glucose monitoring (CGM) sensor. In an embodiment, the blood sugar information may include a blood sugar level of the user, and in some embodiments, may further include information regarding the blood sugar measurement time and method.

In operation S120, the insulin patch control device may input the obtained blood sugar information to a first neural network and may estimate a pump parameter of the insulin patch based on output data from the first neural network. In an embodiment, the first neural network receiving the input of the blood sugar information may estimate an insulin injection amount according to the blood sugar level included in the blood sugar information. In this case, the amount of insulin injected through the insulin patch may be adjusted according to the pump parameter. Therefore, according to an embodiment, the above first neural network receiving blood sugar information may estimate an optimal pump parameter based on blood sugar information obtained in real-time.

In another embodiment, the insulin patch may estimate the pump parameter independently from the insulin patch control device based on measured blood sugar information, and adjust the insulin injection amount based on the estimated pump parameter. That is, the insulin patch control method according to the present embodiment may stably inject insulin to the user even when there is a communication issue between the insulin patch and the insulin patch control device or when an issue occurs in the insulin patch control device. More detailed description will be provided later with reference to FIG. 5.

In operation S130, the insulin patch control device may transmit a control signal to the insulin patch based on the pump parameter estimated in operation S120. In an embodiment, the insulin patch control device and the insulin patch may communicate with each other via a network. As described above, the communication method of the network between the insulin patch control device and the insulin patch is not limited, but in an example, the above network may be a near field wireless communication network, for example, a Bluetooth communication network.

In another embodiment, the insulin patch control device may perform a simulation based on an insulin injection algorithm using the estimated pump parameter before transmitting a control signal to the insulin patch. In addition, the insulin patch control device may re-estimate the pump parameter based on the simulation result. For example, when an expected blood sugar level of the user exceeds an effective range as a result of simulation, the estimated pump parameter may be determined not to be effective, and after that, the pump parameter may be re-estimated by using the above neural network. The accuracy of the insulin patch may be improved through the insulin patch control method according to the present embodiment. This will be described in more detail later with reference to FIG. 6.

In operation S140, the insulin patch control device may obtain control result data from the insulin patch. In an embodiment, the control result data of the insulin patch may include at least one of blood sugar information measured over time, a pump parameter estimated according to the measured blood sugar information, an injection amount of insulin that is injected according to the pump parameter, and blood sugar information after insulin injection. The kind and form of the data included in the control result data of the insulin patch according to some embodiments of the present disclosure are not restricted. For example, the control result data of the insulin patch may be one of time-serial data related to the blood sugar level, time-serial data related to the pump parameter, and time-serial data related to the insulin injection amount, may include data in the form of a pair of the insulin injection amount and the blood sugar level, or may include data in the form of a pair of the pump parameter and the blood sugar level.

In operation S150, the insulin patch control device may input the blood sugar information, the pump parameter, and the control result data of the insulin patch into the second neural network, and in operation S160, the insulin patch control device may estimate pathology diagnosis result data of the user of the insulin patch based on output data from the second neural network. In more detail, the insulin patch control device according to an embodiment may obtain first pathology diagnosis result data by inputting the blood sugar information and the pump parameter into the second neural network, and after that, may perform a feedback with respect to the above first pathology diagnosis result data based on the control result data of the insulin patch. For example, the above second neural network may be re-trained by using the first pathology diagnosis result data and the control result data of the insulin patch. For example, the insulin patch control device may perform reinforcement training of the second neural network by using the control result data of the insulin patch. In this case, the control result data of the insulin patch may include a control signal of the insulin patch based on the pump parameter and blood sugar information according to insulin injection, and may further include information on a diabetes diagnosis result of the user in some embodiments.

In another embodiment, above operations S150 to S160 may be performed by an external server that is connected to the insulin patch control device via the network. In the present embodiment, the external server may include a hospital server or a medical service providing server. In this case, the external server may receive an input of a user feedback signal with respect to the pump parameter of the insulin patch, the simulation result of the insulin patch, or pathology diagnosis result data of the user. In this case, the user may be a user of the hospital server and the medical service providing server, for example, a doctor, a nurse, or a medical staff. After that, the feedback signal of the external server according to some embodiments of the present disclosure may be re-input into the first neural network or the second neural network so as to re-train the neural network.

Figure 4:
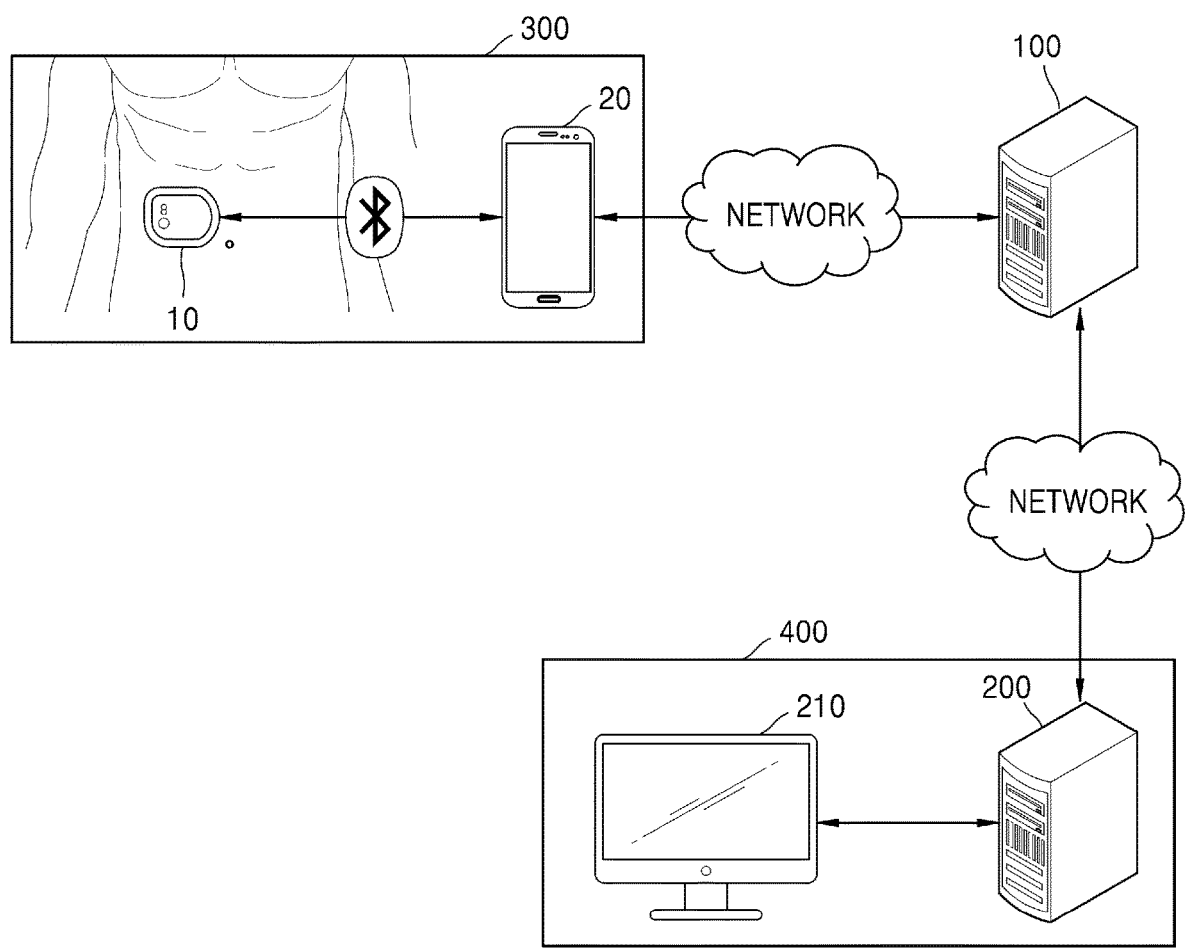
FIG. 4 is an exemplary diagram for describing an insulin patch control system according to an embodiment of the present disclosure.

Hereinafter, a series of processes for controlling an insulin patch according to an embodiment of the present disclosure will be described in detail with reference to FIG. 4.

The insulin patch 10 according to an embodiment of the present disclosure may perform network communication with a user terminal 20 capable of monitoring and/or controlling the insulin patch. In an example, the insulin patch 10 and the user terminal 20 may communicate through Bluetooth communication. The user terminal 20 according to the present embodiment may have an application for monitoring and/or controlling the insulin patch 10 installed thereon, and the user terminal 20 may receive a user input with respect to the insulin patch in real-time via the application. In this case, according to an embodiment, the insulin patch may independently estimate the pump parameter, only when the communication with the user terminal 20, as well as the insulin patch control device 100, is disconnected.

The insulin patch control device 100 according to an embodiment may estimate a pump parameter based on user information of the insulin patch. That is, the insulin patch control device 100 may simultaneously estimate the pump parameters of one or more insulin patches 10 and may estimate the pump parameter of each insulin patch 10 by further using the user information of each insulin patch 10. As such, personalized control of the insulin patch may be possible. Also, the insulin patch control device 100 may create a virtual insulin patch corresponding to each insulin patch and may perform a simulation of the insulin patch by using the estimated pump parameter. Because securing stability of insulin injection is very important, the insulin patch control device 100 according to some embodiments may stably control the insulin patch through the above processes.

According to an embodiment, the external device 200 that obtains the pathology diagnosis result data of the insulin patch user from the insulin patch control device 100 may further include an additional user terminal 210 that may receive a feedback signal with respect to the pathology diagnosis result data. In this case, a user inputting a feedback signal for the pathology diagnosis result data may be a medical staff such as a doctor. As such, the accuracy of the neural network for estimating the pump parameter performed by the insulin patch control device 100 or the external device 200 may be improved.

Figure 5:
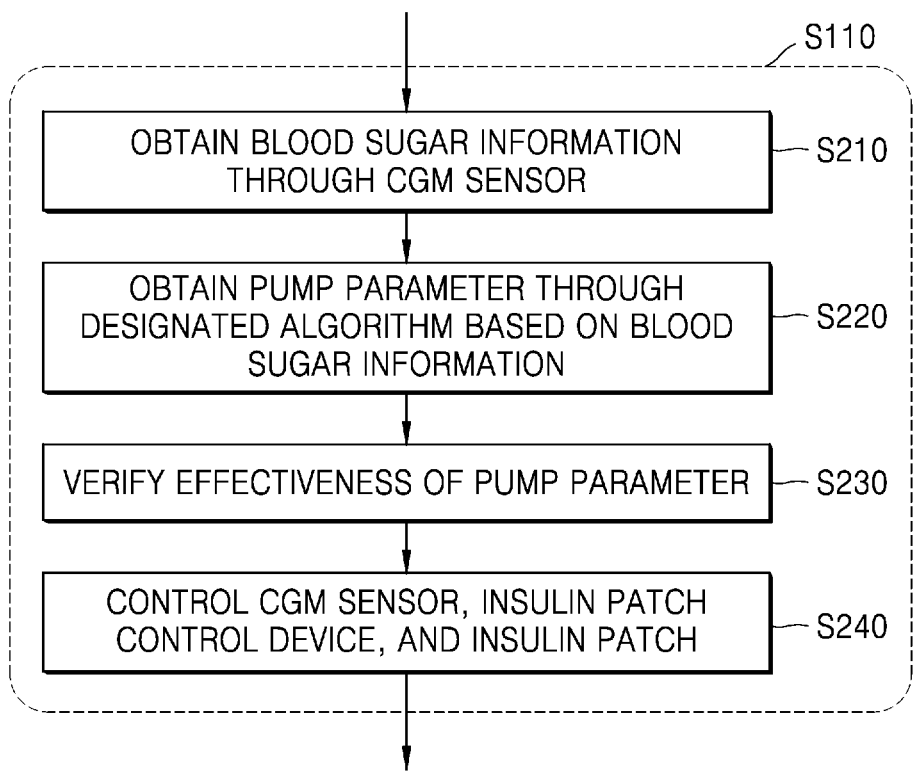
FIGS. 5 to 7 are diagrams for describing some operations in FIG. 3 in detail.
Figure 6:
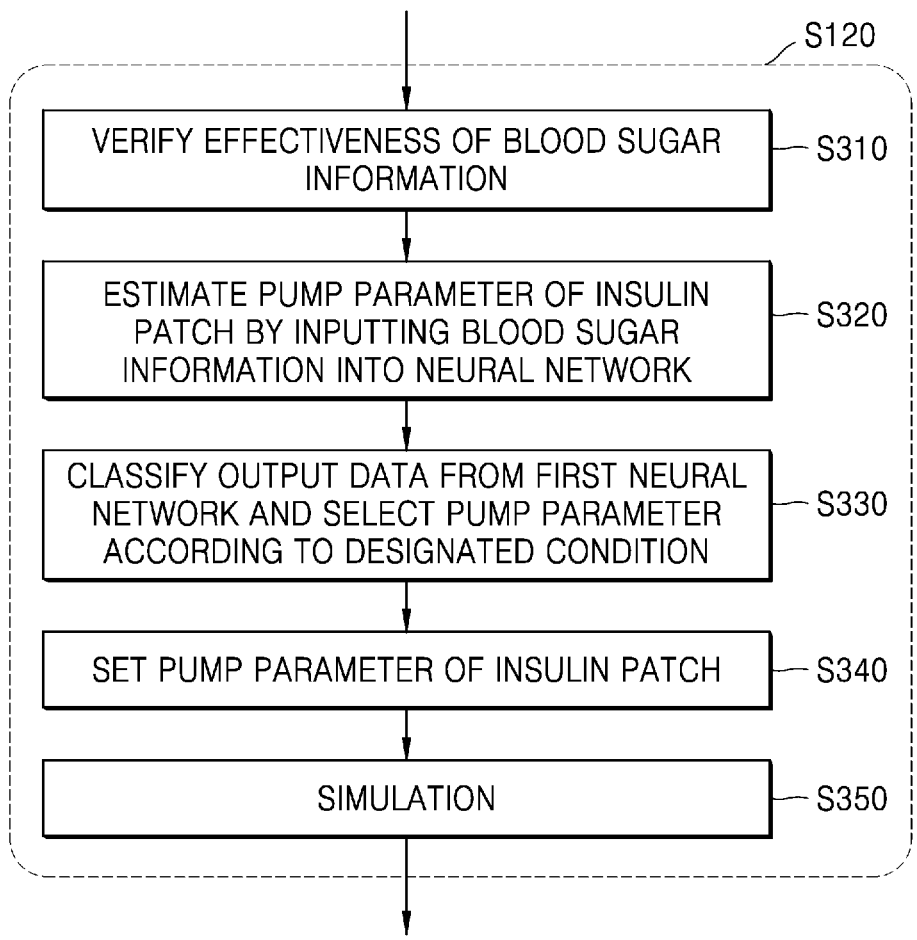
Figure 7:
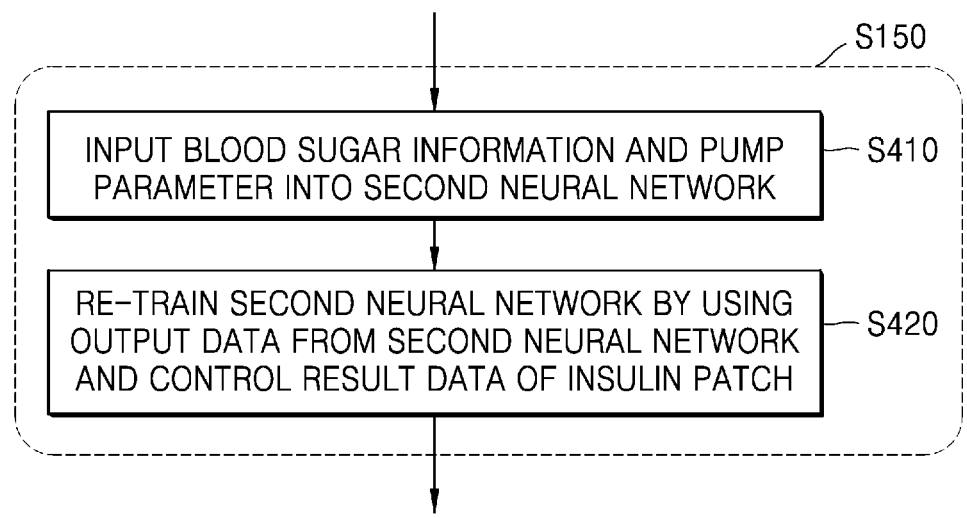

Hereinafter, each process performed by an insulin patch unit 300, the insulin patch control device 100, and a pathology diagnosis result data analysis unit 400 shown in FIG. 4 will be described in detail with reference to FIGS. 5 to 7. A subject performing each of the processes described with reference to FIGS. 5 to 7 is not necessarily limited to a certain electronic device shown in FIG. 4.

Hereinafter, a process of independently estimating a pump parameter, performed by an insulin patch, according to an embodiment of the present disclosure will be described in detail with reference to FIG. 5.

In operation S210, blood sugar information may be obtained through a CGM sensor. However, the CGM sensor is just an example of the blood sugar measurement sensor, and according to some embodiments of the present disclosure, the blood sugar measurement sensor and blood sugar measurement method of the insulin patch are not necessarily restricted to the CGM sensor.

In operation S220, the pump parameter may be obtained through an algorithm designated based on the blood sugar information. In an embodiment, the designated algorithm may be similar to or same as the above-described first neural network, but when the subject of performing operation S220 is the insulin patch, the algorithm may be simplified algorithm having less calculation amount than the first neural network. For example, when an error of a user terminal communicating with an insulin patch, an error of an insulin patch control device, or a communication failure in a network occurs, the insulin patch according to the present embodiment may independently estimate the pump parameter. Accordingly, when the insulin patch according to an embodiment does not receive an insulin patch control signal or pump parameter information from the outside during a specified period of time, the insulin patch may independently estimate the pump parameter for determining the insulin injection amount. That is, the insulin patch according to the present embodiment may independently determine the insulin injection amount without communicating with an external device.

In operation S230, verification of effectiveness of the pump parameter may be performed. That is, before controlling the insulin patch using the obtained pump parameter, a minimum verification of effectiveness for securing stability may be performed. For example, it may be identified whether the obtained pump parameter is within a designated stable range. In this case, the designated stable range may be a fixed value input by the user, a value determined based on previous pump parameter records, or a value estimated through a designated algorithm as in operation S220. In an embodiment, the insulin patch may perform the verification of the effectiveness of the pump parameter, of course, when receiving the control signal of the insulin patch or the pump parameter from the insulin patch control device. That is, in the insulin patch control method according to the present embodiment, the effectiveness of the pump parameter may be verified by the insulin patch that includes the insulin injection portion, not by the insulin patch control device, in order to improve the stability.

In operation S240, the insulin patch may be controlled based on the pump parameter of which the effectiveness has been verified, the CGM sensor and the insulin patch control device may be controlled based on the control result, and the insulin patch control result data may be transmitted to the insulin patch control device. In another embodiment, when the effectiveness of the pump parameter is not verified in operation S230, the above-described operations S210 to S230 may be repeatedly performed.

Hereinafter, a process of performing simulation, performed by the insulin patch control device according to an embodiment of the present disclosure, will be described in detail with reference to FIG. 6.

In operation S310, the insulin patch control device may perform verification of effectiveness of the obtained blood sugar information. The insulin patch control device may perform verification of the effectiveness of the blood sugar information, before inputting the blood sugar information obtained from the insulin patch into the neural network. For example, it may be identified whether the obtained blood sugar information is within an effective range. As such, the insulin patch control device may identify whether there is an error occurring in the insulin patch. The effective range of the blood sugar information may be a fixed value input by the user, a value determined based on past blood sugar information records of each user, or a value estimated through a certain algorithm.

In operation S320, the insulin patch control device may input the blood sugar information to the first neural network in order to estimate the pump parameter of the insulin patch. In an embodiment, the first neural network may be a neural network trained using user's blood sugar information before injecting insulin, an insulin injection amount, an insulin pump parameter, and user's blood sugar information after injecting insulin, or may be a neural network that is transfer-trained using another neural network that is trained by using the insulin injection amount and the blood sugar information. Also, in an embodiment, the first neural network may be a neural network trained by further using user information. As such, the insulin patch control device may estimate the pump parameter by further considering a degree of blood sugar change and speed for each user.

In operation S330, the insulin patch control device may classify the output data from the first neural network and select a pump parameter according to a designated condition from among pump parameters included in the output data. In an embodiment, the designated conditions for selecting a pump parameter may be determined based on user information. For example, the insulin patch control device may select an appropriate pump parameter between a pump parameter for injecting a small amount of insulin for a long period of time and a pump parameter for injecting a large amount of insulin for a short period of time, based on the user information.

In operation S340, the insulin patch control device may set the pump parameter of the insulin patch to be the pump parameter selected in operation S330, and may perform a simulation on a vertical insulin patch through an insulin injection algorithm based on the pump parameter set in operation S350.

In an embodiment, when the expected blood sugar level of the user exceeds the effective range as a result of the simulation, the insulin patch control device may determine that the estimated pump parameter is not effective. In this case, the insulin patch control device may perform a simulation of the insulin patch by using the pump parameter that is not selected in operation S330, and may perform a simulation by using the pump parameter that is re-estimated by repeatedly performing operations S310 to S340. Accuracy and stability of the estimated pump parameters may be improved by the insulin patch control method according to the present embodiment.

Hereinafter, a process of obtaining pathology diagnosis result data according to an embodiment of the present disclosure will be described in detail below with reference to FIG. 7.

In operation S410, the insulin patch control device may input the obtained blood sugar information and the estimated pump parameter to the second neural network.

After that, in operation S420, the insulin patch control device may re-train the second neural network by using the output data from the second neural network and previously obtained control result data of the insulin patch. In an embodiment, the control result data of the insulin patch may include at least one of blood sugar information measured over time, a pump parameter estimated according to the measured blood sugar information, an injection amount of insulin that is injected according to the pump parameter, and blood sugar information after insulin injection.

In more detail, the insulin patch control device according to an embodiment may obtain first pathology diagnosis result data by inputting the blood sugar information and the pump parameter into the second neural network, and after that, may perform a feedback with respect to the above first pathology diagnosis result data based on the control result data of the insulin patch. For example, the above second neural network may be re-trained by using the first pathology diagnosis result data and the control result data of the insulin patch.

For example, the insulin patch control device may perform reinforcement training of the second neural network by using the control result data of the insulin patch. In this case, the control result data of the insulin patch may include a control signal of the insulin patch based on the pump parameter and blood sugar information according to insulin injection, and may further include information on a diabetes diagnosis result of the user in some embodiments.

The device described herein may be implemented using hardware components, software components, and/or combination of the hardware components and the software components. For example, the apparatuses and the components described in the embodiments may be implemented using, for example, a processor, a controller, an arithmetic logic unit (ALU), a digital signal processor, a microcomputer, a field programmable gate array (FPGA), a programmable logic unit (PLU), a microprocessor, or one or more general-purpose computers or specific-purpose computers such as any other device capable of responding to and executing instructions in a defined manner. The processing device may run an operating system (OS) and one or more software applications that run on the OS. The processing device also may access, store, manipulate, process, and create data in response to execution of the software. For convenience of comprehension, the description of a processing device is used as singular; however, one of ordinary skill in the art will be appreciated that a processing device may include multiple processing elements and/or multiple types of processing elements. For example, a processing device may include multiple processors or a processor and a controller. In addition, different processing configurations are possible, such as a parallel processors.

The software may include a computer program, a code, an instruction, or a combination of one or more thereof, for independently or collectively instructing or configuring the processing device to operate as desired. Software and/or data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed manner. The software and data may be stored by one or more computer readable recording media.

The method according to the embodiments may be recorded in non-transitory computer-readable media including program instructions to implement various operations embodied by a computer. The computer-readable media may also include, alone or in combination with the program commands, data files, data structures, etc. The media and program instructions may be those specially designed and constructed for the purposes, or they may be of the kind well-known and available to those of skilled in the computer software arts. Examples of computer-readable media include magnetic media such as hard disks, floppy disks, and magnetic tape; optical media such as CD ROM disks and DVD; magneto-optical media such as floptical disks; and hardware devices that are specially to store and perform program commands, such as read-only memory (ROM), random access memory (RAM), flash memory, etc. Examples of the program commands may include machine language codes generated by a compiler and high-level language codes executable by an interpreter. The aforementioned hardware devices may be configured to operate as one or more software modules to carry out exemplary embodiments, and vice versa.

While the present disclosure has been described with reference to exemplary embodiments, one of ordinary skill in the art may practice various changes and modifications without departing from the spirit and scope of the present disclosure set forth throughout the annexed claim matters. For example, there may be attained a desired result according to the present disclosure even though the techniques are carried out through other methods and procedures different from the aforementioned, and/or even though the system, the structure, the units and the circuits are coupled in other manners different from the aforementioned, or substituted or replaced with other components or equivalents.

Therefore, other implementations, other embodiments, and equivalents of the claims are within the scope of the following claims.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A method of controlling an insulin patch performed by an insulin patch control device comprising: an insulin patch including an insulin pump and a blood sugar sensor; and a computing device that communicates with the insulin patch through a network, the method comprising the steps of:
   obtaining, by the insulin patch, blood sugar information from the blood sugar sensor;
   transmitting the blood sugar information obtained by the insulin patch to the insulin patch control device to input the same to a first neural network of the computing device;
   estimating pump parameters of the insulin patch based on output data from the first neural network;
   simulating the insulin patch by selecting one of the estimated pump parameters;
   in a case where an expected blood sugar level exceeds an effective range as a result of simulation, determining that the estimated pump parameter is not effective, and selecting another pump parameter from among the estimated pump parameters; or re-estimating a pump parameter;
   in a case when an expected blood sugar level exceeds an effective range as a result of simulation, transmitting a control signal to the insulin patch;
   in a case where the insulin patch does not receive the control signal for a specified time due to communication failure of the network or a problem of the insulin patch control device,
   estimating a pump parameter of the insulin patch through an algorithm based on the blood sugar information independently obtained by the insulin patch; and
   transmitting a control signal to the insulin pump based on the estimated pump parameter.

2. The insulin patch control method of claim 1, further comprising the steps of: after the insulin patch control device transmits a control signal to the insulin patch, obtaining, by the insulin patch control device, a control result of the insulin patch from the insulin patch;
   obtaining first pathology diagnosis result data by inputting the obtained blood sugar information into a second neural network;

performing feedback to the second neural network in relation to the first pathology diagnosis result by using a control result of the insulin patch; and estimating the user pathology diagnosis result data of the insulin patch based on output data of the second neural network.

3. The insulin patch control method of claim 2, wherein the step of inputting the obtained blood sugar information into the second neural network comprises the step of:

transmitting the obtained blood sugar information to an external server, and receiving a feedback signal as to an effectiveness of the blood sugar information from the external server, and the step of simulating the insulin patch comprises the step of:

transmitting a simulation result of the insulin patch to the external server, and receiving a feedback signal as to the simulation result of the insulin patch from the external server.

4. The insulin patch control method of claim 2, wherein the insulin patch comprises a blood sugar sensor configured to obtain the pump parameter through a designated algorithm based on the blood sugar information obtained by the blood sugar measurement sensor, verifies an effectiveness of the obtained pump parameter, and generate a control signal.

5. An insulin patch control device comprising
a processor,
wherein the processor is configured to:
obtain blood sugar information measured by a blood sugar sensor, input the obtained blood sugar information to a first neural network, estimate pump parameters of the insulin patch based on output data of the first neural network, and simulate the insulin patch by selecting one of the estimated pump parameters, wherein in a case where an expected blood sugar level exceeds an effective range as a result of simulation, it is determined that the estimated pump parameter is not effective, and another pump parameter is selected from among the estimated pump parameters or a pump parameter is re-estimated, and in a case when an expected blood sugar level is within an effective range as a result of simulation, a control signal is transmitted to the insulin patch, a control result of the insulin patch is obtained from the insulin patch, and the obtained blood sugar information and the estimated pump parameters are transmitted to a second neural network to obtain first pathology diagnosis result data, and then, by using a control result of the insulin patch, feedback is performed to the second neutral network in relation to the first pathology diagnosis result data.

* * * * *